(12) United States Patent
Welch et al.

(10) Patent No.: US 7,968,479 B2
(45) Date of Patent: Jun. 28, 2011

(54) ELASTIC MULTILAYER COMPOSITE INCLUDING PATTERN UNBONDED ELASTIC MATERIALS, ARTICLES CONTAINING SAME, AND METHODS OF MAKING SAME

(75) Inventors: Howard Martin Welch, Woodstock, GA (US); John Joseph Lassig, Dawsonville, GA (US); Wing-Chak Ng, Suwanee, GA (US); Susan Elaine Shawver, Roswell, GA (US); Oomman P. Thomas, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 360 days.

(21) Appl. No.: 12/215,872

(22) Filed: Jun. 30, 2008

(65) Prior Publication Data

US 2009/0324905 A1 Dec. 31, 2009

(51) Int. Cl.
  *D04H 1/00* (2006.01)
  *D04H 13/00* (2006.01)
  *D04H 3/00* (2006.01)
(52) U.S. Cl. ........ 442/328; 442/394; 442/400; 428/198; 156/229; 156/259; 156/290
(58) Field of Classification Search .................. 442/328, 442/394, 400; 428/198; 156/290, 229, 259
  See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,855,046 A | 12/1974 | Hansen et al. | |
| 4,323,534 A | 4/1982 | DesMarais | |
| 4,340,563 A | 7/1982 | Appel et al. | |
| 4,494,629 A | 1/1985 | Raeburn | |
| 4,522,203 A | 6/1985 | Mays | |
| 4,652,487 A | 3/1987 | Morman | |
| 4,655,760 A | 4/1987 | Morman et al. | |
| 4,657,802 A | 4/1987 | Morman | |
| 4,663,220 A | 5/1987 | Wisneski et al. | |
| 4,704,116 A | 11/1987 | Enloe | |
| 4,720,415 A | 1/1988 | VanderWielen et al. | |
| 4,725,473 A * | 2/1988 | Van Gompel et al. | 428/156 |
| 4,734,324 A | 3/1988 | Hill | |
| 4,781,966 A | 11/1988 | Taylor | |
| 4,789,699 A | 12/1988 | Kieffer et al. | |
| 4,798,603 A | 1/1989 | Meyer et al. | |
| 4,834,738 A | 5/1989 | Kielpikowski et al. | |
| 4,842,596 A | 6/1989 | Kielpikowski et al. | |
| 4,937,299 A | 6/1990 | Ewen et al. | |
| 4,965,122 A | 10/1990 | Morman | |
| 4,981,747 A | 1/1991 | Morman | |
| 5,093,422 A | 3/1992 | Himes | |
| 5,114,781 A | 5/1992 | Morman et al. | |
| 5,116,662 A | 5/1992 | Morman | |
| 5,176,668 A | 1/1993 | Bernardin | |
| 5,176,672 A | 1/1993 | Bruemmer et al. | |
| 5,192,606 A | 3/1993 | Proxmire et al. | |
| 5,218,071 A | 6/1993 | Tsutsui et al. | |
| 5,226,992 A | 7/1993 | Morman | |
| 5,272,236 A | 12/1993 | Lai et al. | |
| 5,278,272 A | 1/1994 | Lai et al. | |
| 5,288,791 A | 2/1994 | Collier, IV et al. | |
| 5,304,599 A | 4/1994 | Himes | |
| 5,322,728 A | 6/1994 | Davey et al. | |
| 5,332,613 A | 7/1994 | Taylor et al. | |
| 5,336,545 A | 8/1994 | Morman | |
| 5,382,400 A | 1/1995 | Pike et al. | |
| 5,385,775 A | 1/1995 | Wright | |
| 5,399,219 A | 3/1995 | Roessler et al. | |
| 5,472,775 A | 12/1995 | Obijeski et al. | |
| 5,486,166 A | 1/1996 | Bishop et al. | |
| 5,490,846 A | 2/1996 | Ellis et al. | |
| 5,509,915 A | 4/1996 | Hanson et al. | |
| 5,514,470 A | 5/1996 | Haffner et al. | |
| 5,539,056 A | 7/1996 | Yang et al. | |
| 5,540,796 A | 7/1996 | Fries | |
| 5,540,976 A | 7/1996 | Shawver et al. | |
| 5,571,619 A | 11/1996 | McAlpin et al. | |
| 5,595,618 A | 1/1997 | Fries et al. | |
| 5,596,052 A | 1/1997 | Resconi et al. | |
| 5,681,645 A | 10/1997 | Strack et al. | |

(Continued)

FOREIGN PATENT DOCUMENTS

EP 0691203 A1 1/1996

(Continued)

OTHER PUBLICATIONS

Lawrence, K.D. et al., "An Improved Device for the Formation of Superfine, Thermoplastic Fibers", *NRL Report 5265*, Feb. 11, 1959.
Wente, V.A. et al., "Manufacture of Superfine Organic Fibers", *NRL Report 4364*, May 25, 1954.
INDA IST-70.4-99 IST 70.4 (99), "Standard Test Method for Water Vapor Transmission Rate Through Non Woven and Plastic Film Using a Guard Film and Vapor Pressure Sensor", 1999.
Federal Test Method Standard No. 191A, Method 5514, "Water Resistance of Cloth; Low Range, Hydrostatic Pressure Method", Jul. 1978.

*Primary Examiner* — Norca L Torres-Velazquez (74) *Attorney, Agent, or Firm* — Richard M. Shane (57) ABSTRACT

An elastic multilayer composite includes a pattern unbonded elastic layer attached to at least one extensible facing layer. A method for forming an elastic multilayer composite includes the steps of providing an elastic material; bonding the elastic material to form a pattern unbonded elastic material; and attaching the pattern unbonded elastic material to at least one facing material.

22 Claims, 5 Drawing Sheets

U.S. PATENT DOCUMENTS

| | | | |
|---|---|---|---|
| 5,695,849 A | 12/1997 | Shawver et al. | |
| 5,714,107 A | 2/1998 | Levy et al. | |
| 5,858,515 A | 1/1999 | Stokes et al. | |
| 5,882,769 A | 3/1999 | McCormack et al. | |
| 5,883,028 A | 3/1999 | Morman et al. | |
| 5,952,252 A | 9/1999 | Shawver et al. | |
| 5,962,112 A | 10/1999 | Haynes et al. | |
| 6,057,024 A | 5/2000 | Mleziva et al. | |
| 6,090,234 A | 7/2000 | Barone et al. | |
| 6,090,325 A | 7/2000 | Wheat et al. | |
| 6,096,668 A | 8/2000 | Abuto et al. | |
| 6,111,163 A | 8/2000 | McCormack et al. | |
| 6,114,596 A | 9/2000 | Nayak et al. | |
| 6,176,952 B1 | 1/2001 | Maugans et al. | |
| 6,309,736 B1 | 10/2001 | McCormack et al. | |
| 6,475,600 B1 | 11/2002 | Morman et al. | |
| 6,500,563 B1 | 12/2002 | Datta et al. | |
| 6,730,390 B1 * | 5/2004 | Kobayashi et al. | 428/198 |
| 6,909,028 B1 | 6/2005 | Shawver et al. | |
| 6,992,159 B2 | 1/2006 | Datta et al. | |
| 7,078,089 B2 | 7/2006 | Ellis et al. | |
| 7,220,478 B2 | 5/2007 | McCormack et al. | |
| 2003/0124310 A1 | 7/2003 | Ellis et al. | |
| 2005/0095943 A1 * | 5/2005 | Griffin et al. | 442/352 |
| 2006/0003658 A1 | 1/2006 | Hall et al. | |
| 2006/0052023 A1 | 3/2006 | Lauridsen et al. | |
| 2006/0148358 A1 * | 7/2006 | Hall et al. | 442/328 |

FOREIGN PATENT DOCUMENTS

| | | |
|---|---|---|
| EP | 0712892 A1 | 5/1996 |
| EP | 0989222 B1 | 6/2007 |
| WO | WO 95/16425 | 6/1995 |
| WO | WO 95/16562 | 6/1995 |
| WO | WO 96/19346 | 6/1996 |
| WO | WO 97/30843 | 8/1997 |
| WO | WO 98/29479 | 7/1998 |
| WO | WO 00/38918 | 7/2000 |

* cited by examiner

ELASTIC MULTILAYER COMPOSITE INCLUDING PATTERN UNBONDED ELASTIC MATERIALS, ARTICLES CONTAINING SAME, AND METHODS OF MAKING SAME

BACKGROUND OF THE INVENTION

Elastic multilayer composites are useful in a wide variety of applications including use as personal care product bodyside facing liner material (or topsheets), outercovers, waist elastic materials, side panel materials, ear materials, containment flaps, leg elastics (gasketing) and hook and loop fastening materials. Various elastic multilayer composites have been formed by bonding an elastic layer to one or more facing layers to form either a stretch bonded laminate, a neck bonded laminate or a neck stretch bonded laminate. Stretch bonded laminate materials offer machine direction stretch and recovery properties. Neck bonded laminates offer cross-machine direction stretch and recovery properties. Neck stretch bonded laminates offer stretch and recovery properties in both the cross-machine and machine directions.

Various types of elastic layers have been utilized in the production of elastic multilayer composites, such as elastic films, strands, foams, fibers or fibrous webs, and so forth. Despite all of these types of elastic layers, there remains a need for improved elastic multilayer composites that have good elastic properties (for example, reduced hysteresis and/or permanent set). Other desirable properties include good breathability, good barrier properties, and an acceptable price point. There is also a need for efficient methods of manufacturing such materials which do not hamper the elastic performance of the materials produced. It is to such desires that the current invention is directed.

SUMMARY OF THE INVENTION

The present invention is directed to elastic multilayer composites, methods of making elastic multilayer composites, and articles containing elastic multilayer composites. In particular, an elastic multilayer composite includes a first extensible facing material and a pattern unbonded elastic layer attached to the facing material. The pattern unbonded elastic layer includes a continuous bonded region defining a plurality of discreet, fibrous regions that are less bonded than the continuous bonded region. The extensible facing desirably does not include a continuous bonded region corresponding to the elastic layer continuous bonded region. In another embodiment, the extensible facing desirably does not include the same bond pattern as the elastic layer.

In one embodiment, the continuous bonded region is bonded to the extent that it forms a continuous film. Desirably, the elastic layer comprises an extruded meltblown web of fibers. Optionally, the elastic multilayer composite may include a second extensible facing material attached to the pattern unbonded elastic layer such that the pattern unbonded elastic layer is positioned between the first and second extensible facing materials. The facing materials may include, for example, breathable or nonbreathable films, or nonwoven fabrics such as spunbond or meltblown webs, or combinations of the same. The elastic multilayer composite may be extensible and elastic in either the machine direction, the cross-machine direction, or both.

In another aspect, a method of making an elastic multilayer composite includes the steps of forming an elastic fibrous fabric; feeding the elastic fibrous fabric into a nip defined between a first roller having a patterned outer surface and an oppposedly positioned second roller having a smooth outer surface; bonding the elastic fibrous fabric to form on a surface thereof a continuous bonded region defining a plurality of discrete fibrous regions to form a pattern unbonded elastic sheet; and attaching a first facing material to the pattern unbonded elastic sheet. In one embodiment the bonding of the elastic fibrous fabric to form on a surface thereof a continuous bonded region is accomplished by application of heat and/or pressure. Desirably the elastic fibrous fabric comprises an extruded meltblown web. Optionally, a second facing material may be attached to the pattern unbonded elastic sheet wherein the pattern unbonded elastic sheet is positioned between the first and second facing materials. In one embodiment, the method further includes the step of stretching the pattern unbonded elastic sheet by from about 10% to about 500% prior to attaching the first facing material to the pattern unbonded elastic sheet. The stretching may occur in any dimension, most suitably in either the cross direction, the machine direction, or both. In a further embodiment, the first facing material may include a film. The film may be breathable, and may include slits and/or apertures. In an even further embodiment, the method may further include the step of necking the first facing material prior to attaching the first facing material to the pattern unbonded elastic sheet.

DEFINITIONS

The term "nonwoven fabric or web" means a web having a structure of individual fibers or threads which are interlaid, but not in an identifiable manner as in a knitted or woven fabric. Nonwoven fabrics or webs can be formed from many processes such as for example, meltblowing processes, spunbonding processes, bonded carded web processes, and so forth.

The term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns.

The term "spunbond fibers" refers to small diameter microfibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802, 817 to Matsuki et al., U.S. Pat. Nos. 3,338,992 and 3,341,394 to Kinney, U.S. Pat. No. 3,502,763 to Hartman, U.S. Pat. No. 5,382,400 to Pike et al., and U.S. Pat. No. 3,542,615 to Dobo et al, each incorporated by reference herein in its entirety. Spunbond fibers are generally not tacky when they are deposited onto a collecting surface. Spunbond fibers are generally continuous and have average diameters (from a sample of at least 10) larger than 7 microns, more particularly, between about 10 and 20 microns.

The term "meltblown" means fibers/microfibers formed by extruding a molten thermoplastic material through a plurality of fine, usually circular die capillaries as molten threads or filaments into converging high velocity gas (e.g. air) streams which attenuate the filaments of molten thermoplastic material to reduce their diameter to microfiber diameter. Thereafter, the meltblown fibers are carried by the high velocity gas stream and are deposited on a collecting surface to form a web of randomly dispersed meltblown fibers. Such a process is disclosed, in various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; and U.S. Pat. No. 3,849,241, issued Nov. 19, 1974, to Butin, et al, which patent is incorporated by reference hereto in its entirety. Meltblown fibers are microfibers which may be continuous or discontinuous, are generally smaller than 10 microns in average diameter, and are usually tacky when deposited onto a collecting surface.

As used herein, the term "melt spinning" shall mean a process in which a fiber forming substance is melted and extruded into air or other gas, where it is cooled and solidified.

As used herein the term "set" refers to retained elongation in a material sample following an elongation and recovery, i.e. after the material has been stretched and allowed to relax during a cycle test. The term "permanent set" refers to the retained set following a period of 1 minute after retraction.

As used herein the term "thermal point bonding" involves passing a fabric or web of fibers to be bonded through the application of heat and pressure such as between a heated calender roll and an anvil roll. The calender roll is usually, though not always, patterned in some way so that the entire fabric is not bonded across its entire surface, and the anvil roll is usually smooth. As a result, various patterns for calender rolls have been developed for functional as well as aesthetic reasons. One example of a pattern has points and is the Hansen Pennings or "H&P" pattern with about a 30 percent bond area with about 200 bonds/square inch as taught in U.S. Pat. No. 3,855,046 to Hansen and Pennings, incorporated herein by reference hereto in its entirety.

As used herein "pattern unbonded" means a fabric having continuous bonded regions defining a plurality of discrete unbonded regions. The fibers or filaments within the discrete unbonded regions are dimensionally stabilized by the continuous bonded regions that encircle or surround each unbonded region. The unbonded regions are specifically designed to afford spaces between fibers or filaments within the unbonded regions. A suitable process for forming a pattern-unbonded nonwoven material includes providing a fibrous fabric or web, providing oppositely positioned first and second calender rolls and defining a nip therebetween, with one or both of the rolls being heated as necessary and having a bonding pattern on its outermost surface comprising a continuous pattern of land areas defining a plurality of discrete openings, apertures or holes, and passing the fabric or web within the nip formed by the rolls. Each of the openings in the roll or rolls defined by the continuous land areas forms a discrete unbonded region in at least one surface of the nonwoven fabric or web in which the fibers or filaments of the web are substantially or completely unbonded. Stated alternatively, the continuous pattern of land regions in said roll or rolls forms a continuous pattern of bonded regions that define a plurality of discrete unbonded regions on at least one surface of the fabric or web.

As used herein, the term "breathable" refers to a material which is permeable to water vapor. The water vapor transmission rate (WVTR) or moisture vapor transfer rate (MVTR) is measured in grams per square meter per 24 hours, and shall be considered equivalent indicators of breathability. The term "breathable" desirably refers to a material which is permeable to water vapor having a minimum WVTR (water vapor transmission rate) of desirably about 300 $g/m^2/24$ hours. The WVTR of a fabric, in one aspect, gives an indication of how comfortable a fabric would be to wear. WVTR is measured as indicated below.

"Neck bonding" refers to the process wherein an elastic member is bonded to a non-elastic member while only the non-elastic member is extended or necked so as to reduce its dimension in the direction orthogonal to the extension. "Neck bonded laminate" refers to a composite elastic material made according to the neck bonding process, i.e., the layers are joined together when only the non-elastic layer is in an extended condition. Such laminates usually have cross directional stretch properties. Further examples of neck-bonded laminates are such as those described in U.S. Pat. Nos. 5,226,992, 4,981,747, 4,965,122 and 5,336,545 to Morman and U.S. Pat. No. 5,514,470 to Haffner et al., each of which is incorporated by reference herein in its entirety.

"Stretch bonding" refers to a process wherein an elastic member is bonded to another member while only the elastic member is extended, such as by at least about 25 percent of its relaxed length. "Stretch bonded laminate" refers to a composite elastic material made according to the stretch bonding process, i.e., the layers are joined together when only the elastic layer is in an extended condition so that upon relaxing the layers, the nonelastic layer is gathered. Such laminates usually have machine directional stretch properties and may be subsequently stretched to the extent that the nonelastic material gathered between the bond locations allows the elastic material to elongate. One type of stretch bonded laminate is disclosed, for example, by U.S. Pat. No. 4,720,415 to Vander Wielen et al., in which multiple layers of the same polymer produced from multiple banks of extruders are used. Other suitable composite elastic materials are disclosed in U.S. Pat. No. 4,789,699 to Kieffer et al., U.S. Pat. No. 4,781,966 to Taylor and U.S. Pat. Nos. 4,657,802 and 4,652,487 to Morman and U.S. Pat. No. 4,655,760 to Morman et al., as well as U.S. Pat. No. 5,385,775 to Wright, each of the foregoing being incorporated by reference herein in its entirety.

"Neck-stretch bonding" generally refers to a process wherein an elastic member is bonded to another member while the elastic member is extended such as by at least about 25 percent of its relaxed length and the other layer is a necked, non-elastic layer. "Neck-stretch bonded laminate" refers to a composite elastic material made according to the neck-stretch bonding process, i.e., the layers are joined together when both layers are in an extended condition and then allowed to relax. Such laminates usually have multi-directional stretch properties.

The terms "elastic" and "elastomeric" when referring to a fiber, film or nonwoven fabric mean a material which upon application of a biasing force, is stretchable in at least one direction by at least 50% to a stretched, biased length which is at least 50% greater than its relaxed, unstretched length, and which will recover at least 50 percent of its elongation upon release of the stretching, biasing force after 1 minute (and under ambient conditions). The term "extensible" means elongatable or stretchable in at least one direction.

The term "recover" or "retract" refers to a relaxation of a stretched material upon removal of a biasing force following stretching of the material by application of the biasing force. For example, if a material having a relaxed, unbiased length of one (1) inch was elongated 50 percent by stretching to a length of one and one half (1.5) inches, the material would have a stretched length that is 50% greater than its relaxed length. If this exemplary stretched material contracted, that is recovered to a length of one and one tenth (1.1) inches after release of the biasing and stretching force, the material would have recovered 80 percent (0.4 inch) of its elongation.

The term "garment" means any type of non-medically oriented apparel which may be worn. This includes industrial or protective workwear like coveralls, labcoats, undergarments, pants, shirts, jackets, gloves, socks, and so forth.

The term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and so forth.

The term "personal care products" shall be used interchangeably with "absorbent articles" and means diapers, training pants, absorbent underpants, adult incontinence products, swimwear, feminine hygiene products, and mortuary and veterinary absorbent products.

As used herein, the terms "machine direction" or MD means the direction along the length of a fabric or other web or film in the direction in which it is produced. The terms "cross-machine direction," "cross directional," or CD mean the direction across the width of fabric, i.e. a direction generally perpendicular to the MD.

As used herein, and in the claims, the term "comprising" is inclusive or open-ended and does not exclude additional unrecited elements, compositional components, or method steps. Accordingly, such term is intended to be synonymous with the words "has", "have", "having", "includes", "including", and any derivatives of these words. Additionally, the term "comprising" encompasses the more restrictive terms "consisting essentially of" and "consisting of."

Test Method Procedures

Stress-Strain Cycle Test (2 Cycle to 100% Elongation, $3^{rd}$ Elongation to Break):

An elastic fabric, film, or multilayer composite (laminate) sample of 7.62 centimeters wide and 15.24 centimeters long is placed in the clamps of a constant rate of extension (CRE) load frame, such as a SINTECH tensile tester commercially available from the MTS Systems Corporation, model Synergie 200, Eden Prairie, Minn. Starting at a 7.62 centimeters gauge length between the sample grips, the sample is elongated at 500 mm/minute to 100% elongation (15.24 centimeter jaw-span). The cross-head returns to the original 7.62 centimeters gauge length position to complete each cycle. Two full cycles to 100% elongation are performed, followed by a third elongation to break. The data points are recorded and plotted in grams force on the Y axis and % elongation on the X axis. Percent set is determined as the percent elongation at which the specimen reaches zero load on the return portion (i.e. retraction) of the cycle. Testing is conducted at approximately 23° C. and about 50 percent relative humidity.

For percent hysteresis calculations, the data is acquired at a rate of 100 data points per cycle. The loading and unloading energy are calculated by integrating the area under the respective curves. The lower % hysteresis values correspond to better elastic efficiency of the composite measured. Percentage hysteresis is calculated according to the following equation.

% HYSTERESIS=[(LOADING ENERGY−UNLOADING ENERGY)/LOADING ENERGY]×100

Water Vapor Transmission Rate (WVTR)/Breathability:

A suitable technique for determining the WVTR (water vapor transmission rate) value of a film, fabric, or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. This information is used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:

WVTR: The calculation of the WVTR uses the formula:

$$WVTR = F p_{sat}(T) RH / (A p_{sat}(T)(1-RH))$$

where:

F=The flow of water vapor in cc/min.,
$p_{sat}(T)$=The density of water in saturated air at temperature T,
RH=The relative humidity at specified locations in the cell,
A=The cross sectional area of the cell, and,
$p_{sat}(T)$=The saturation vapor pressure of water vapor at temperature T.

For the purposes of this Application, the testing temperature for the above test should be at about 37.8° C., the flow is about 100 cc/min, and the relative humidity is about 60%. Additionally, the value for n should be equal to 6 and the number of cycles should be 3.

Hydrostatic Head/Barrier:

A measure of the liquid barrier properties of a film, fabric, or laminate material is the hydrostatic head test. The hydrostatic head test determines the height of water (in centimeters) which the fabric will support before a predetermined amount of liquid passes through. A fabric with a higher hydrostatic head reading indicates it has a greater barrier to liquid penetration than a fabric with a lower hydrostatic head. The hydrostatic head test is performed according to Federal Test Standard 191A, Method 5514.

The test is modified to include a screen support of standard synthetic fiber window screen material. The test head of a Textest FX-300 Hydrostatic Head Tester, available from Schmid Corporation, having offices in Spartanburg, S.C. is filled with purified water. The purified water is maintained at a temperature between about 18.3° C. and 29.4° C., which is within the range of normal ambient conditions (about 23° C.) and about 50% relative humidity). An 8 inch by 8 inch (about 20.3 cm by 20.3 cm) square sample of the test material is placed such that the test head reservoir is covered completely. The sample is subjected to a standardized water pressure, increased at a constant rate until leakage is observed on the outer surface of the sample material. Hydrostatic pressure resistance is measured at the first sign of leakage (droplets) in three separate areas of the sample, excluding the edges of the sample. This test is repeated for forty specimens of each sample material. The hydrostatic pressure resistance results for each specimen are averaged and recorded in millibars. Again, a higher value indicates greater resistance to water penetration and is desirable for barrier applications.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Figure 1:
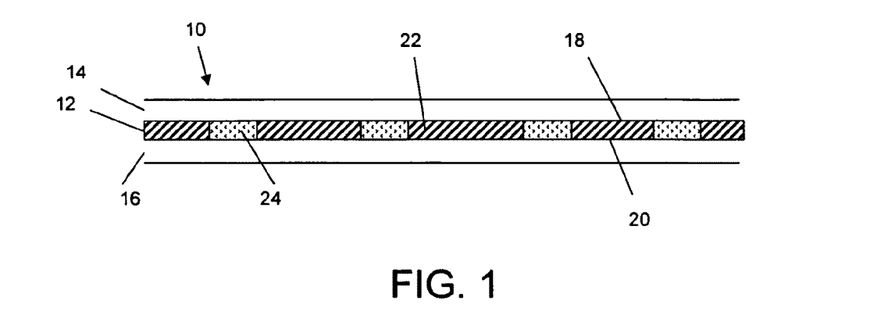
FIG. 1 is a cross-sectional side view of the elastic multilayer composite of FIG. 2.
Figure 2:
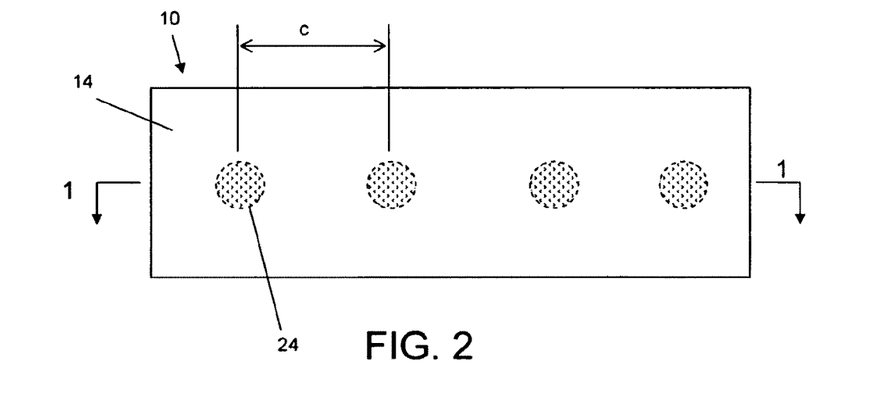
FIG. 2 is a top elevational view of an elastic multilayer composite having a pattern unbonded elastic layer in accordance with one embodiment of the present invention.

Referring to FIGS. 1 and 2, an elastic multilayer composite 10 includes a pattern unbonded elastic layer 12, a first extensible facing layer 14, and an optional second extensible facing layer 16. The pattern unbonded elastic layer 12 has a first side 18 and a second side 20. The first extensible facing layer 14 is attached to the first side 18 of the pattern unbonded elastic layer 12. Optionally, a second extensible facing layer 16 may be attached to the second side 20 of the pattern unbonded elastic layer 12.

Figure 6:
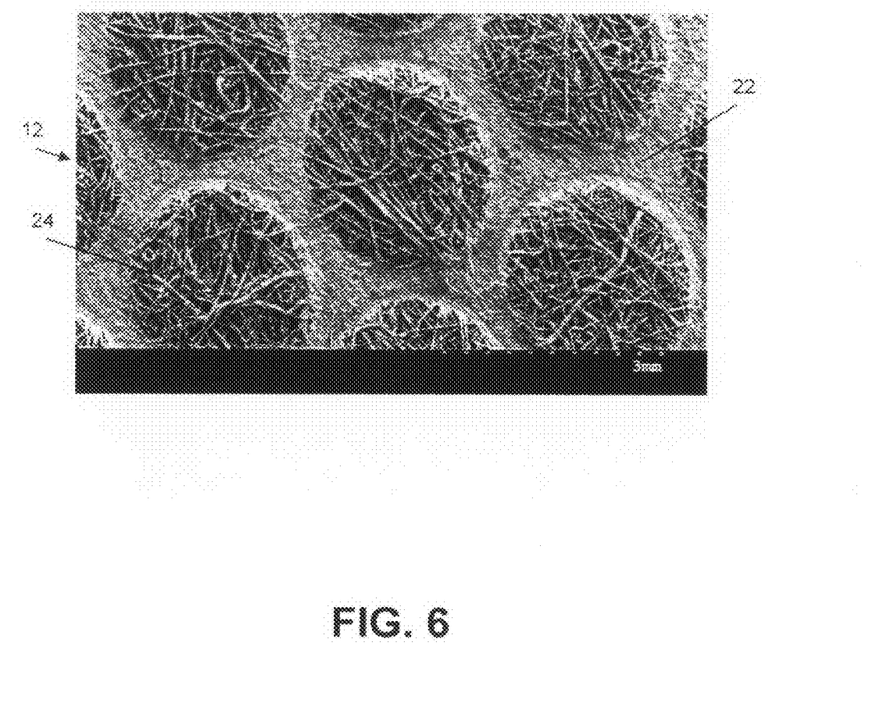
FIG. 6 is an SEM photomicrograph of an exemplary pattern bonded elastic layer that can be used in accordance with an embodiment of the present invention.

Referring additionally to FIG. 6, the pattern unbonded elastic layer 12 desirably comprises a layer of elastic polymeric fibers formed from an elastic polymer composition. The pattern unbonded elastic layer 12 is desirably a fibrous fabric or web having continuous bonded regions 22 that define a plurality of discreet, dimensionally stabilized unbonded fibrous regions 24. Within the continuous bonded regions 22, the fibers or filaments of the web are desirably pressed, joined, attached, bonded, or fused together, and more desirably are fully bonded or fused together so as to be a film or non-fibrous or film-like region, whereas within the discrete unbonded regions 24 the fibers or filaments of the nonwoven fabric or web retain their fibrous structure and are desirably autogenously bonded together while retaining their fibrous structure. The continuous bonded regions 22 are generally bonded to a greater extent than the discrete unbonded regions 24. In another embodiment, one surface or side 18 of the continuous bonded regions 22 may be glazed, or film-like, while the opposite surface or side 20 of the pattern unbonded elastic layer 12 nearest to the unheated roll may remain fibrous. The elastic layer 12 may be formed from a variety of known fibrous materials, including but not limited to woven materials, scrim materials, nonwoven materials including but not limited to spunbonded webs, meltblown webs, airlaid webs, wetlaid webs, coform webs, hydraulically entangled webs, bonded carded webs, and so forth. The basis weight of the elastic layer may range from about 10 to about 160 grams per square meter, in some embodiments from about 15 to about 100 grams per square mater, and in some embodiments from about 20 to about 60 grams per square meter.

Desirably, the continuous bonded regions 22 of the pattern unbonded elastic layer 12 are bonded prior to the pattern unbonded elastic layer being laminated to the other facing layer(s) 14, 16. The pattern unbonded elastic layer provides an efficient elastic structure without affecting properties of the facing layers such as may occur if the entire composite is pattern unbonded. So as to not affect the properties of the extensible facing, the extensible facing desirably does not include a continuous bonded region corresponding to the elastic layer continuous bonded region. In another aspect, the extensible facing desirably does not include the same bond pattern as the elastic layer. Without being bound to a particular theory, it is believed that the bonding between the fibers in the continuous bonded regions 22 promotes improved elastic behavior of the elastic multilayer composite 10 by reducing the amount of fiber slippage that occurs in the bonded regions when the elastic multilayer composite is extended during use. Because less slippage occurs in the continuous bonded regions, it is expected that increasing the ratio of the continuous bonded region area (size) to the unbonded region area will improve elastic behavior as reflected by reduced hysteresis and permanent set measurements. Additionally, adjustment of the bond area may also provide a mechanism for controlling breathability and barrier properties of the elastic multilayer composite. As can be seen in FIG. 6, the continuous bonded regions 22 are more film-like and therefore are expected to have reduced breathability and improved barrier compared to the more open structure of the discrete fibrous regions. Therefore, increasing the ratio of the bonded region area to the unbonded region area will reduce breathability and improve barrier properties of the elastic multilayer composite.

The elastic polymer composition desirably comprises thermoplastic elastomeric polymer and optionally may further include a tackifier or other bonding aid to improve adhesion between the pattern unbonded elastic layer 12 and the opposed facing layer(s) 14, 16. Any of a variety of thermoplastic elastomeric polymers may generally be employed in the present invention, such as elastomeric polyesters, elastomeric polyurethanes (PU), elastomeric polyamides, elastomeric copolymers, elastomeric polyolefins, ethylene-vinyl acetate (EVA), EPDM rubbers, ethylene-ethyl acrylate (EEA), ethylene acrylic acid (EEA), ethylene methyl acrylate (EMA), polyamide polyether block copolymers, block copolymers having the general formula A-B-A' or A-B like copoly(styrene/ethylene-butylene), styrene-poly(ethylene-propylene)-styrene, styrenepoly(ethylene-butylene)-styrene, and so forth.

In one embodiment, for instance, a substantially amorphous block copolymer may be employed that contains blocks of a monoalkenyl arene and a conjugated diene such as a saturated conjugated diene. The monoalkenyl arene block(s) may include styrene and its analogues and homologues, such as o-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene block(s) may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth. The amount of monoalkenyl arene (e.g., polystyrene) blocks may vary, but typically constitute from about 8 wt. % to about 55 wt. %, in some embodiments from about 10 wt. % to about 35 wt. %, and in some embodiments, from about 25 wt. % to about 35 wt. % of the copolymer. Suitable block copolymers may contain monoalkenyl arene endblocks having a number average molecular weight from about 5,000 to about 35,000 and saturated conjugated diene midblocks having a number average molecular weight from about 20,000 to about 170,000. The total number average molecular weight of the block polymer may be from about 30,000 to about 250,000.

Other suitable thermoplastic elastomeric copolymers are available from Kraton Polymers LLC of Houston, Tex. under the trade name KRATON®. KRATON® polymers include styrene-diene block copolymers, such as styrene-butadiene, styrene-isoprene, styrene-butadiene-styrene, and styrene-isoprene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These block copolymers may have a linear, radial or star-shaped molecular configuration. Specific KRATON® block copolymers include those sold under the brand names G 1652, G 1657, G 1730, MD6673, and MD6973. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Of course, other thermoplastic elastomeric polymers may also be used to form the pattern unbonded elastic layer, either alone or in conjunction with the block copolymers. Semi-crystalline polyolefins, for example, may be employed that have or are capable of exhibiting a substantially regular structure. Exemplary semi-crystalline polyolefins include polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group).

Particularly suitable polyethylene copolymers are those that are "linear" or "substantially linear." The term "substantially linear" means that, in addition to the short chain branches attributable to comonomer incorporation, the ethylene polymer also contains long chain branches in that the polymer backbone. "Long chain branching" refers to a chain length of at least 6 carbons. Each long chain branch may have the same comonomer distribution as the polymer backbone and be as long as the polymer backbone to which it is attached. In contrast to the term "substantially linear", the term "linear" means that the polymer lacks measurable or demonstrable long chain branches. That is, the polymer is substituted with an average of less than 0.01 long chain branch per 1000 carbons.

The density of a linear ethylene/α-olefin copolymer is a function of both the length and amount of the α-olefin. That is, the greater the length of the α-olefin and the greater the amount of α-olefin present, the lower the density of the copolymer. Although not necessarily required, linear polyethylene "plastomers" are particularly desirable in that the content of α-olefin short chain branching content is such that the ethylene copolymer exhibits both plastic and elastomeric characteristics—i.e., a "plastomer." Because polymerization with α-olefin comonomers decreases crystallinity and density, the resulting plastomer normally has a density lower than that of polyethylene thermoplastic polymers (e.g., LLDPE), but approaching and/or overlapping that of an elastomer. For example, the density of the polyethylene plastomer may be 0.91 grams per cubic centimeter ($g/cm^3$) or less, in some embodiments, from 0.85 to 0.88 $g/cm^3$, and in some embodiments, from 0.85 $g/cm^3$ to 0.87 $g/cm^3$. Despite having a density similar to elastomers, plastomers generally exhibit a higher degree of crystallinity, are relatively non-tacky, and may be formed into pellets that are non-adhesive and relatively free flowing.

Suitable polyethylenes include ethylene-based copolymer plastomers available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai et al.; and U.S. Pat No. 5,278,272 to Lai, et al., which are incorporated herein in their entirety by reference thereto for all purposes.

Propylene plastomers may also be suitable for use in the pattern unbonded elastic layer. Suitable plastomeric propylene polymers may include, for instance, copolymers or terpolymers of propylene include copolymers of propylene with an α-olefin (e.g., $C_3$-$C_{20}$), such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. Preferably, the density of the polypropylene (e.g., propylene/α-olefin copolymer) may be 0.91 grams per cubic centimeter (g/cm$^3$) or less, in some embodiments, from 0.85 to 0.88 g/cm$^3$, and in some embodiments, from 0.85 g/cm$^3$ to 0.87 g/cm$^3$. Suitable propylene polymers are commercially available under the designations VISTAMAXX™ from ExxonMobil Chemical Co.; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes.

Any of a variety of known techniques may generally be employed to form the semi-crystalline polyolefins. For instance, olefin polymers may be formed using a free radical or a coordination catalyst (e.g., Ziegler-Natta). Preferably, the olefin polymer is formed from a single-site coordination catalyst or a constrained geometry catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al., which are incorporated herein in their entirety by reference thereto for all purposes. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

Besides elastomeric polymers, generally inelastic thermoplastic polymers may also be included so long as they do not adversely affect the elasticity of the composite. For example, the thermoplastic composition may contain other polyolefins (e.g., polypropylene, polyethylene, etc.). In one embodiment, the thermoplastic composition may contain an additional propylene polymer, such as homopolypropylene or a copolymer of propylene. The additional propylene polymer may, for instance, be formed from a substantially isotactic polypropylene homopolymer or a copolymer containing equal to or less than about 10 wt. % of other monomer, i.e., at least about 90% by weight propylene. Such a polypropylene may be present in the form of a graft, random, or block copolymer and may be predominantly crystalline in that it has a sharp melting point above about 110° C., in some embodiments about above 115° C., and in some embodiments, above about 130° C. Examples of such additional polypropylenes are described in U.S. Pat. No. 6,992,159 to Datta, et al., which is incorporated herein in its entirety by reference thereto for all purposes.

As mentioned above, other additives may also be incorporated into the pattern unbonded elastic layer, such as melt stabilizers, crosslinking catalysts, radiation cross-linking promoter (pro-rad) additives, processing stabilizers, heat stabilizers, light stabilizers, antioxidants, heat aging stabilizers, whitening agents, antiblocking agents, bonding agents, tackifiers, viscosity modifiers, etc. Examples of suitable tackifier resins may include, for instance, hydrogenated hydrocarbon resins. REGALREZ™ hydrocarbon resins are examples of such hydrogenated hydrocarbon resins, and are available from Eastman Chemical. Other tackifiers are available from ExxonMobil under the ESCOREZ™ designation. Viscosity modifiers may also be employed, such as polyethylene wax (e.g., EPOLENE™ C-10 from Eastman Chemical). Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant. Some suitable hindered phenols include those available from Ciba Specialty Chemicals of under the trade name "Irganox®", such as Irganox® 1076, 1010, or E 201. Moreover, bonding agents may also be added to the pattern unbonded elastic layer to facilitate bonding of the pattern unbonded elastic layer to additional materials (e.g., nonwoven web). Typically, such additives (e.g., tackifier, antioxidant, stabilizer, etc.) are each present in an amount from about 0.001 wt. % to about 25 wt. %, in some embodiments, from about 0.005 wt. % to about 20 wt. %, and in some embodiments, from 0.01 wt. % to about 15 wt. % of the pattern unbonded elastic layer.

In addition to the pattern unbonded elastic layer, the elastic multilayer composite also includes at least one extensible facing layer attached to the pattern unbonded elastic layer. The facing layer may be selected from any of a variety of extensible facing layers as is known in the art, such as films, foams, woven fabrics, meshed fabrics, scrims, loosely woven fabrics, nonwoven web materials, for example, meltblown webs, spunbond webs, bonded carded webs, wetlaid webs, airlaid webs, coform webs, hydraulically entangled webs, and so forth, and laminates thereof. The facing layer may be extensible prior to being attached to the pattern unbonded elastic layer. Examples of suitable extensible facing layers are described in U.S. Pat. No. 4,965,122 to Morman et al.; U.S. Pat. No. 5,114,781 to Morman et al.; U.S. Pat. No. 5,336,545 to Morman et al.; U.S. Pat. No. 4,720,415 to Vander Wielen et al.; U.S. Pat. No. 4,789,699 to Kieffer et al.; U.S. Pat. No. 5,332,613 to Taylor et al.; U.S. Pat. No. 5,288,791 to Collier et al.; U.S. Pat. No. 4,663,220 to Wisneski et al.; U.S. Pat. No. 5,540,976 to Shawver et al.; U.S. Pat. No. 5,952,252 to Shawver et al.; U.S. Pat. No. 5,714,107 to Levy et al.; and European Application No. 0, 712,892 A1 to Djiaw et al.; the entire contents of which are incorporated herein by reference. The composition of the facing layer may be selected as desired to achieve a material having the desired properties, such as elasticity, hand, tensile strength, cost etc. Further, the outer nonwoven layer may be treated such as, for example, by embossing, hydroentangling, mechanical softening, printing, anti-static treatment or treated in an other manner in order to achieve desired aesthetics and/or functional characteristics.

Alternatively, the facing layer may be made extensible in the process of attaching the facing layer to the pattern unbonded elastic layer, such as, for example, by stretch-bonding, neck bonding, neck-stretch bonding, grooved rolling, or incremental stretching. The basis weight of the facing layer may range from about 1 to about 60 grams per square meter, in some embodiments from about 2 to about 40 grams per square mater, and in some embodiments from about 3 to about 30 grams per square meter.

For example, in a stretch bonding process, the pattern unbonded elastic layer may be bonded to a gathered nonwoven web, such as described in U.S. Pat. No. 4,720,415 to Vander Wielen et al., the contents of which are incorporated herein by reference for all purposes. Such elastic composite materials can be made by (a) tensioning or stretching the pattern unbonded elastic layer (which may comprise an extruded meltblown web of elastomeric fibers) to elongate it; (b) bonding the elongated elastic pattern unbonded elastic layer to at least one gatherable web (which can comprise a nonwoven web such as a spunbond fiber web) under conditions which soften at least portions of the pattern unbonded elastic layer to form a bonded multilayer composite; and (c) relaxing the bonded multilayer composite after the bonding step whereby the gatherable web is gathered to form the elastic multilayer composite.

If an extensible film is used as a facing layer, the extensible film may comprise either a mono-layer or multi-layer film. In addition, non-porous and microporous films are believed suitable. The film may comprise a barrier layer and may also exhibit good drape; such films desirably have a basis weight between about 10 grams per square meter and 100 grams per square meter and, even more desirably, between about 15 grams per square meter and 60 grams per square meter. Thermoplastic polymers used in the fabrication of the films may include, but are not limited to, polyolefins including homopolymers, copolymers, terpolymers and blends thereof. In addition, flexible polyolefin films may be used. Additional film forming polymers which may be used, alone or in combination with other polymers, include ethylene vinyl acetate (EVA), ethylene ethyl acrylate (EEA), ethylene acrylic acid (EAA), ethylene methyl acrylate (EMA), ethylene normal butyl acrylate (EnBA), polyurethane (PU), poly(ether-ester) and poly(amid-ether) block copolymers. Elastomeric polyolefin polymers may be used such as, for example, polymers of ethylene and propylene as well as copolymers, terpolymers and blends thereof; examples include, but are not limited to, elastomeric polyolefins and ethylene-propylene copolymer blends.

In one embodiment, the film may comprise a breathable barrier comprising such as, for example, microporous films having a WVTR of at least 300 grams per square meter per day, and more desirably having a WVTR in excess of 600 grams per square meter per day or 1000 grams per square meter per day. Often, for breathable barriers useful in personal care products, safety garments, and medical products desirably have higher WVTRs and breathable barriers of the present invention can have WVTRs exceeding about 2000 $g/m^2/24$ hours, 3000 $g/m^2/24$ hours, 5,000 $g/m^2/24$ hours or even exceeding 8,000 $g/m^2/24$ hours. Breathable microporous film can be formed by any one of various methods known in the art. As an example, the breathable barrier film can comprise a stretched filled-film which includes a thermoplastic polymer and filler. These (and other) components can be mixed together, heated and then extruded into a monolayer or multilayer film. The filled film may be made by any one of a variety of film forming processes known in the art such as, for example, by using either cast or blown film equipment. The thermoplastic polymer and filler can be stretched in at least one direction, thereby reducing the film gauge or thickness and creating a network of micropores of a size and frequency to achieve the desired level of breathability. Examples of breathable barrier films suitable for use with the present invention are described in WO 95/16562 filed Jun. 22, 1995 to McCormack; WO 96/19346 filed Jun. 27, 1996 to McCormack et al.; EP0691203A1 to McCormack et al.; WO98/29479 to Gwaltney et al; U.S. Pat. No. 6,111,163 McCormack et al.; U.S. Pat. No. 6,309,736 to McCormack et al.; U.S. Pat. No. 6,909,028 to Shawver et al.; U.S. Pat. No. 7,220,478 to McCormack et al.; the entire content of the aforesaid references are incorporated herein by reference. Such films, prior to stretching, desirably have a basis weight of less than about 100 grams per square meter and even more desirably less than about 60 grams per square meter. Upon stretching the multilayer film desirably has a basis weight of less than 60 grams per square meter and even more desirably between about 15 and 35 grams per square meter. Suitable films can also include multilayer films such as, for example, those formed by co-extrusion; see for example the methods of forming multilayer films as disclosed in U.S. Pat. Nos. 4,522,203; 4,494,629; and 4,734,324 the entire contents of which are incorporated herein by reference.

Figure 3:
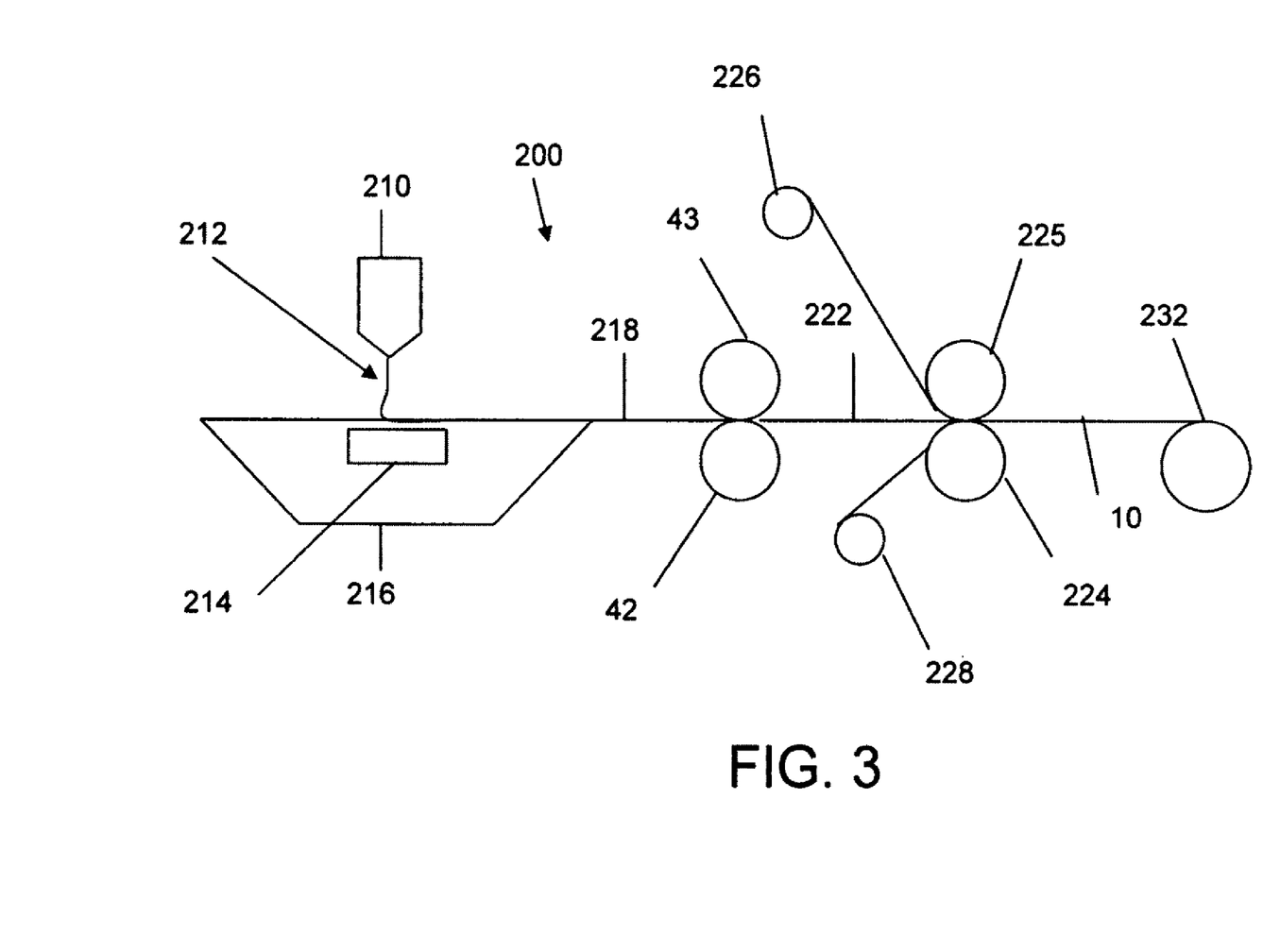
FIG. 3 schematically illustrates a manufacturing process for making elastic multilayer composites in accordance with one embodiment of the present invention.

A process 200 for producing an elastic multilayer composite 10 in accordance with the invention is illustrated in FIG. 3. A nonwoven (for example, meltblown or spunbond) extrusion bank 210, as well known in the art, generates elastic fibers or filaments 212, though other fiber forming processes may be utilized. The elastic fibers or filaments 212 are deposited on a continuous forming surface 216 in a random manner, generally assisted by a vacuum device 214 placed beneath the forming surface. The purpose of the vacuum is to eliminate the undesirable scattering of the filaments and guide the filaments onto the forming surface to form a uniform nonwoven web of elastic filaments 218. If desired, the resultant web 218 can be lightly bonded by a compression roller or hot air jet or stream (not shown) before the web is subjected to a pattern unbonding assembly 42, 43. Alternatively, a web of elastic filaments may be unwound from a roll as elastic material 218 before being subjected to the pattern unbonding assembly 42, 43.

Figure 4:
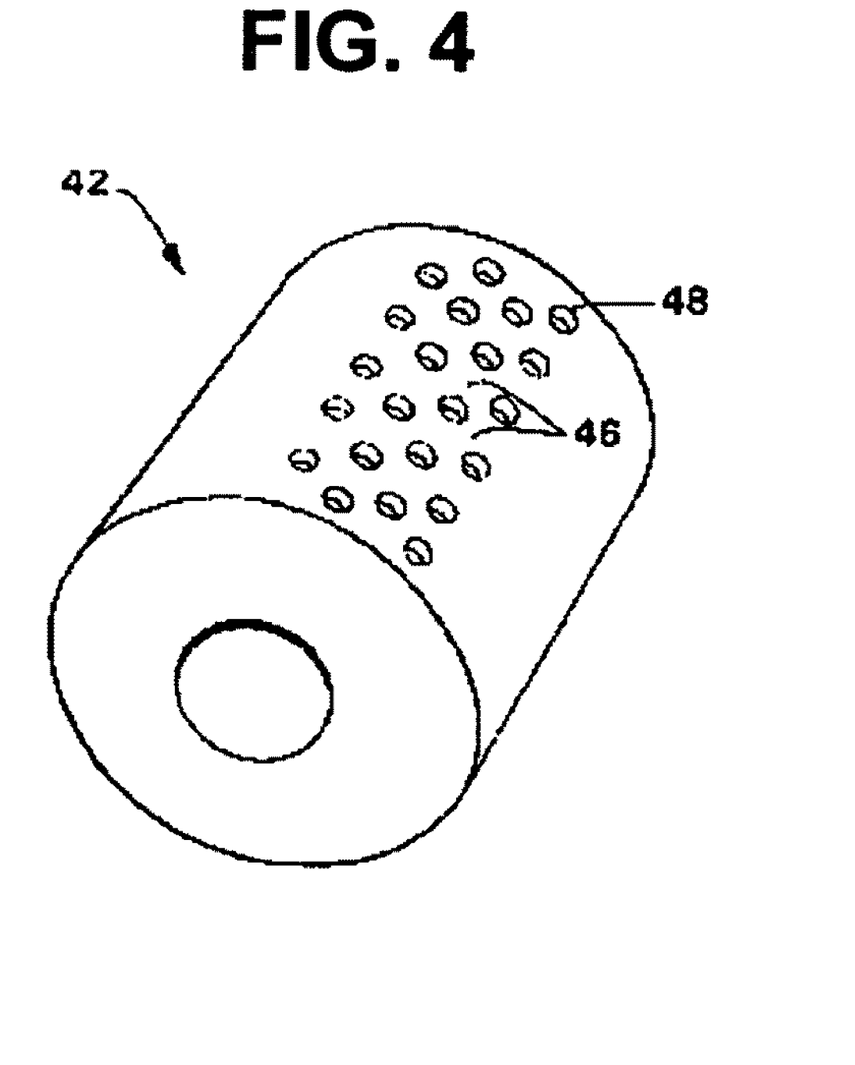
FIG. 4 is a partial perspective view of a pattern roll that can be used in accordance with the process and apparatus of FIG. 3

The elastic web 218 may be transferred directly from the forming surface 216 to a first nip formed between a first set of counter-rotating pattern unbonded rollers 42, 43 as described herein. The pattern unbonding assembly includes a pattern roll or roller 42 and an anvil (or smooth) roll 43. Referring to FIG. 4, the pattern roll 42 is a right circular cylinder that may be formed of any suitable, durable material, such as, for example, steel, to reduce wear on the rolls during use. The pattern roll 42 has on its outermost surface a pattern of land regions or areas 46 that define a plurality of discrete openings or apertures 48. The pattern of openings 48 desirably extends around the circumference of the roll (though not depicted as such in FIG. 4), though other patterns such as shown may be used to provide zones with different stretch or other properties. The land regions 46 are designed to form a nip with the smooth or flat outer surface of oppositely positioned anvil roll 43, which also is a right circular cylinder that can be formed of any suitable, durable material.

The size, shape, number and configuration of the openings 48 in the pattern roll 42 can be varied as described above to meet the particular end use needs of the pattern unbonded elastic layer in the elastic multilayer composite being formed thereby. The desirability of restricting the size of the openings 48 in the pattern roll 42, and the unbonded regions 24 formed thereby in the pattern unbonded elastic layer 12 (and improving the elasticity and barrier), is counter balanced by the extent to which the elastic multilayer composite is to remain breathable. The circular openings 48 and corresponding unbonded regions 24 may have diameters ranging from about 1 to about 10 millimeters, desirably ranging from about 1.5 to about 5 millimeters. The density of the openings 48 in the pattern roll 42 and the unbonded regions 24 formed thereby in the pattern unbonded elastic layer may desirably range from about 0.1 openings per square centimeter to about 25 openings per square centimeter, more desirably from about 1 to about 15 openings per square centimeter, and even more desirably from about 2 to about 10 openings per square centimeter. Suitable inter-opening spaces and corresponding spaces between unbonded regions 24 can range from about 1 to about 10 millimeters centerline-to-centerline, in the machine and cross-machine directions, desirably from about 2 to about 9 millimeters, more desirably from about 3 to about 8 millimeters. The centerline-to-centerline distance is depicted as dimension "c" in FIG. 2. While the openings 48 in pattern roll 42 as shown in FIG. 4, and the corresponding unbonded regions 24, are circular, other shapes, such as ovals, squares, diamonds and so forth can be advantageously employed.

As described above, the portion of the outermost surface of the pattern roll 42 occupied by continuous land regions 46 can be modified depending on the contemplated end-use application of the elastic multilayer material. The degree of bonding imparted to the pattern unbonded elastic layer by the continuous land regions 46 can be expressed as a percent bond area, which refers to the portion of the total plan area of at least one surface of the pattern unbonded elastic layer 12 that is occupied by continuous bonded regions 14. Percent bond area may range from about 15 to about 90 percent, and even more, desirably from about 20 to about 80 percent, more desirably from about 25 to about 70 percent.

The temperature of the outer surface of the pattern roll 42 and the anvil roll 43 can be varied by heating or cooling, which can affect the degree of bonding achieved. Additionally or alternatively, the nip pressure between the pattern roll 42 and the anvil roll 43 can be varied to affect the degree of bonding achieved. For example, heating only one of the pattern roll and the anvil roll may result in one side of the elastic material nearest to the heated roll becoming glazed or film-like, while the side of the elastic material nearest to the unheated roll will remain fibrous. As another example, both surfaces of the continuous bonded regions may be glazed or film-like regions, while a fibrous region may remain between the bonded surfaces of the continuous bonded region. The thickness of the glazed or film-like regions on one or both surfaces may extend from the surface of the continuous bonded region to about 10% through the thickness of the continuous bonded region, or to about 30% through the thickness of the continuous bonded region, or to about 50% through the thickness of the continuous bonded region, or to about 75% through the thickness of the continuous bonded region, or to 100% through the thickness of the continuous bonded region.

After exiting the nip between the pattern roll 42 and the anvil roll 43, a pattern unbonded elastic material 222 and the facing materials 226, 228 may be adhered through a bonding step, such as through adhesive bonding, thermal bonding, point bonding, pressure bonding, ultrasonic bonding, hydroentangling, and so forth. As depicted in FIG. 3, the pattern unbonded elastic material 222 and the facing materials 226, 228 may be directed to a second nip formed between a second set of counter-rotating bond rollers 224, 225 where the pattern unbonded elastic material 222 is attached (bonded or laminated) to one or more facing materials 226, 228. In some embodiments, the pattern unbonded elastic material 222 may be stretched (extended) in the machine direction from about 10% to about 500%, or from about 50% to about 400%, for example) as it is bonded to the facing materials 226, 228. The stretching may occur in any dimension, most suitably in either the cross direction, the machine direction, or both. In another aspect, the stretching may be done prior to applying the pattern unbending to the elastic material whereafter the stretching is maintained through the attachment to one or more facing materials. When the pattern unbonded elastic material 222 is stretched in the machine direction as it is bonded to the facing material 226, 228, the resulting elastic multilayer composite 10 may be allowed to retract to form a stretch bonded laminate. Alternatively, the pattern unbonded elastic material 222 may be drawn by tenter frame, grooved rolls, incremental stretching apparatus, or other device (not shown) in the cross-direction to provide cross-direction retraction and elasticity. As a further alternative, the pattern unbonded elastic material may be stretched simultaneously in both the machine and cross directions. Finally, the elastic multilayer composite 10 may be wound onto a roll 232 for storage.

Apparatuses and processes useful for making pattern unbonded nonwoven fabrics are described in U.S. Pat. No. 5,858,515 to Stokes et al., which is incorporated herein in its entirety by reference thereto for all purposes.

Figure 5:
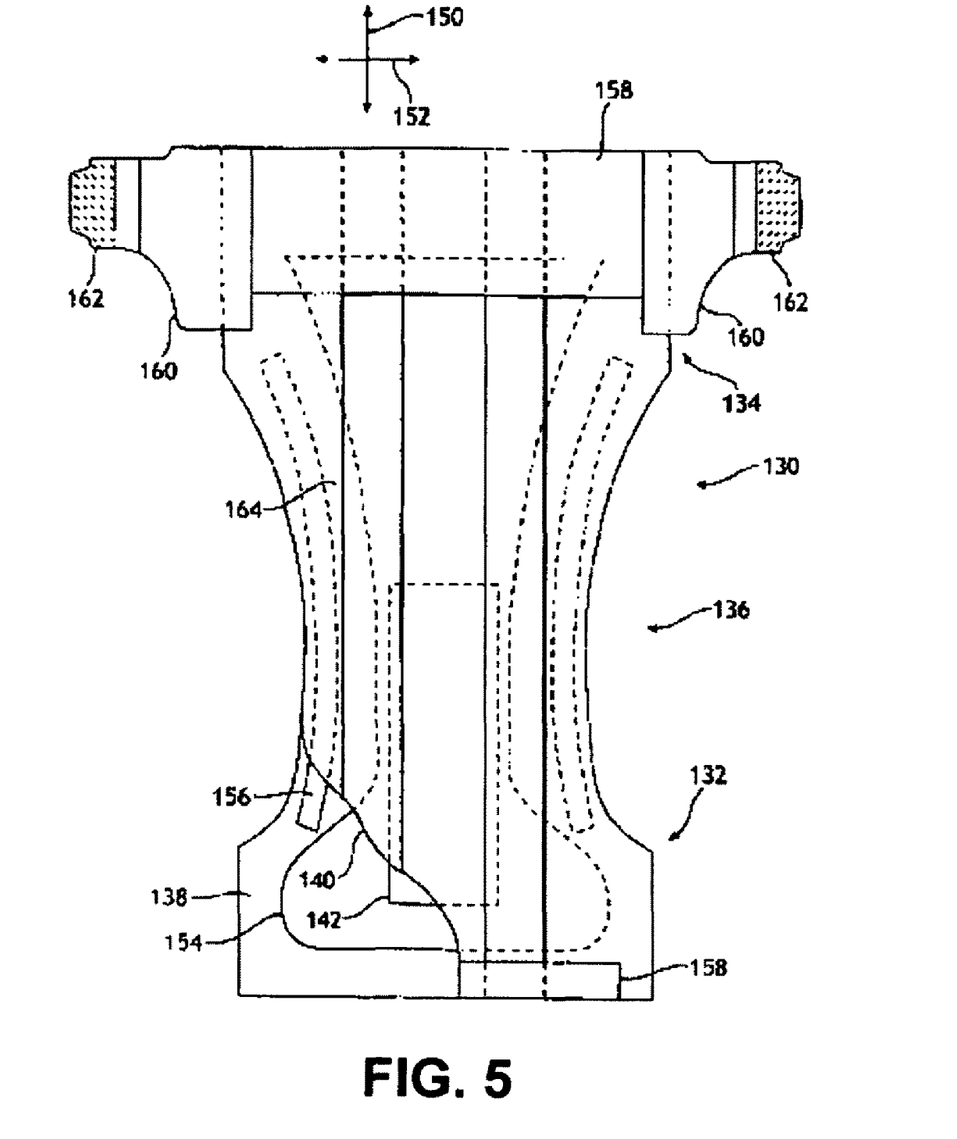
FIG. 5 is a perspective view of a personal care product that may be formed in accordance with one embodiment of the present invention.

The elastic multilayer composites can be incorporated into a variety of absorbent articles, and other consumer oriented products, such as garments, including medical garments and safety garments, personal care products, infection control products and wipes, such as wet or moistened wipes. For the purposes of example only, and not designed to be limiting, a personal care product is shown in FIG. 5, incorporating elastic multilayer composites of the invention. In particular, a diaper is illustrated in FIG. 5.

The elastic multilayer composites may be useful in personal care articles such as by providing elastic waist, gasketing (such as leg elastics), stretchable ear, side panel, stretchable outer cover, containment flap, stretchable liner, and hook and loop material applications. FIG. 5 is presented to illustrate such various components of a diaper that may take advantage of such materials. With specific reference to FIG. 5, the disposable diaper 130 generally defines a front waist section 132, a rear waist section 134, and an intermediate section 136 which interconnects the front and rear waist sections. The front and rear waist sections 132 and 134 include the general portions of the diaper which are constructed to extend substantially over the wearer's front and rear abdominal regions, respectively, during use. The intermediate section 136 of the diaper includes the general portion of the diaper that is constructed to extend through the wearer's crotch region between the legs. Thus, the intermediate section 136 is an area where repeated liquid surges typically occur in the diaper.

The diaper 130 includes, without limitation, an outer cover, or backsheet 138, a liquid permeable bodyside liner, or topsheet, 140 positioned in facing relation with the backsheet 138, and an absorbent core body, or liquid retention structure, 154, such as an absorbent pad, which is located between the backsheet 138 and the topsheet 140. The backsheet 138, which may optionally be extensible or elastic, defines a length, or longitudinal direction 150, and a width, or lateral direction 152 which, in the illustrated embodiment, coincide with the length and width of the diaper 130. The liquid retention structure 154 generally has a length and width that are less than the length and width of the backsheet 138, respectively. Thus, marginal portions of the diaper 130, such as marginal sections of the backsheet 138, may extend past the terminal edges of the liquid retention structure 154. In the illustrated embodiment, for example, the backsheet 138 extends outwardly beyond the terminal marginal edges of the liquid retention structure 154 to form side margins and end margins of the diaper 130. The topsheet 140 is generally coextensive with the backsheet 138 but may optionally cover an area which is larger or smaller than the area of the backsheet 138, as desired.

To provide improved fit and to help reduce leakage of body exudates from the diaper 130, the diaper side margins and end margins may be elasticized with suitable elastic members, as further explained below. For example, as representatively illustrated in FIG. 5, the diaper 130 may include leg elastics 156 which are constructed to operably tension the side margins of the diaper 130 to provide elasticized leg bands which can closely fit around the legs of the wearer to reduce leakage (gasketing) and provide improved comfort and appearance. Waist elastics 158 are employed to elasticize the end margins of the diaper 130 to provide elasticized waistbands. The waist elastics 158 are configured to provide a resilient, comfortably close fit around the waist of the wearer.

The elastic multilayer composites of the invention are suitable for use as the leg elastics 156 and waist elastics 158. Exemplary of such materials are portions of the elastomeric multilayer composite which are adhered to the backsheet, such that elastic constrictive forces are imparted to the backsheet 138.

As is known, fastening means, such as hook and loop fasteners, may be employed to secure the diaper 130 on a wearer. Alternatively, other fastening means, such as buttons, pins, snaps, adhesive tape fasteners, cohesives, fabric-and-loop fasteners, or the like, may be employed. The inventive material may be used, as fastening material, such as hook and loop loop-like materials. In the illustrated embodiment, the diaper 130 includes a pair of side panels 160 (or ears) to which the fasteners 162, indicated as the hook portion of a hook and loop fastener, are attached. Generally, the side panels 160 are attached to the side edges of the diaper 130 in one of the waist sections 132, 134 and extend laterally outward therefrom. The side panels 160 may also be elasticized or otherwise rendered elastomeric by use of the inventive elastic multilayer composite. Examples of absorbent articles that include elasticized side panels and selectively configured fastener tabs are described in PCT Patent Application No. WO 95/16425 to Roessler; U.S. Pat. No. 5,399,219 to Roessler et al.; U.S. Pat. No. 5,540,796 to Fries; and U.S. Pat. No. 5,595,618 to Fries each of which is hereby incorporated by reference in its entirety.

The diaper 130 may also include a surge management layer 142, located between the topsheet 140 and the liquid retention structure, to rapidly accept fluid exudates and distribute the fluid exudates to the liquid retention structure 154 within the diaper 130. The diaper 130 may further include a ventilation layer (not illustrated), also called a spacer, or spacer layer, located between the liquid retention structure 154 and the backsheet 138, to insulate the backsheet 138 from the liquid retention structure 154 to reduce the dampness of the garment at the exterior surface of a breathable outer cover, or backsheet, 138. Examples of suitable surge management layers 142 are described in U.S. Pat. No. 5,486,166 to Bishop and U.S. Pat. No. 5,490,846 to Ellis.

As representatively illustrated in FIG. 5, the disposable diaper 130 may also include a pair of containment flaps 164 which are configured to provide a barrier to the lateral flow of body exudates. The containment flaps 164 may be located along the laterally opposed side edges of the diaper 130 adjacent the side edges of the liquid retention structure 154. Each containment flap 164 typically defines an unattached edge which is configured to maintain an upright, perpendicular configuration in at least the intermediate section 136 of the diaper 130, to form a seal against the wearer's body. The containment flaps 164 may extend longitudinally along the entire length of the liquid retention structure 154 or may only extend partially along the length of the liquid retention structure. When the containment flaps 164 are shorter in length than the liquid retention structure 154, the containment flaps 164 can be selectively positioned anywhere along the side edges of the diaper 130 in the intermediate section 136. The construction of such containment flaps 164 are generally well known to those skilled in the art. For example, suitable constructions and arrangements for containment flaps 164 are described in U.S. Pat. No. 4,704,116 to K. Enloe, incorporated by reference herein in its entirety. The material of the present invention may also serve as the base material for such containment flaps.

The diaper 130 may be of various suitable shapes. For example, the diaper may have an overall rectangular shape, T-shape or an approximately hour-glass shape. In the shown embodiment, the diaper 130 has a generally I-shape. Other suitable components which may be incorporated on absorbent articles of the present invention may include waist flaps and so forth which are generally known to those skilled in the art. Examples of diaper configurations suitable for use in connection with the instant invention which may include other components suitable for use on diapers are described in U.S. Pat. No. 4,798,603 to Meyer et al.; U.S. Pat. No. 5,176,668 to Bernardin; U.S. Pat. No. 5,176,672 to Bruemmer et al.; U.S. Pat. No. 5,192,606 to Proxmire et al. and U.S. Pat. No. 5,509,915 to Hanson et al. each of which is hereby incorporated by reference herein in its entirety.

The various components of the diaper 130 are assembled together employing various types of suitable attachment means, such as adhesive, ultrasonic bonds, thermal bonds or combinations thereof. In the shown embodiment, for example, the topsheet 140 and backsheet 138 may be assembled to each other and to the liquid retention structure 154 with lines of adhesive, such as a hot melt, pressure-sensitive adhesive. Similarly, other diaper components, such as the elastic members 156 and 158, fastening members 162, and surge layer 142 may be assembled into the article by employing the above-identified attachment mechanisms. The elastic multilayer composites of the present invention may be utilized for many of the above described materials where elastic performance (stretch and recovery) is desired. Additionally,

EXAMPLES

The inventive materials and methods of making them are exemplified by the following examples. As with the figures, the examples are not meant to be limiting.

A series of elastic multilayer composites with pattern bonded elastic meltblown were made by laminating a pattern bonded elastic meltblown material to facing materials including polypropylene spunbond webs (SB)(10-20 grams per square meter with , breathable films (18-20 grams per square meter), and/or adhesively laminated spunbond/film laminates (aSFL). From a first meltblown bank, an approximate basis weight of 140 grams per square meter of KRATON® G2755 polymer (a styrenic block copolymer compound including a tackifier and processing aid) or 70% KRATON® G2755 polymer/30% VISTAMAXX™ 2330 olefinic based elastomer was meltblown onto a forming wire at 17 feet per minute to form a meltblown elastic web. The meltblown elastic web was transferred directly from the forming wire to a first nip formed between a first set of counter-rotating pattern unbonded rollers as described herein. The pattern roller had a pattern similar to that illustrated by the pattern unbonded nonwoven material shown in the photomicrograph of FIG. 6. The pattern roll and anvil roll with the pattern unbonded pattern were unheated. The nip pressure within the nip was 150 pounds per linear inch. Control samples were prepared by opening the nip so as to not bond the elastic meltblown material.

After passing the first bonding station (the pattern unbonded bonding station), the elastic meltblown was directed to a second nip formed between a second set of counter-rotating bond rollers (both rollers were smooth rollers) where the meltblown elastic web was bonded to one or more facing materials. In some examples, the meltblown elastic web was stretched (extended) in the machine direction (3×, for example) as it entered the second nip to be bonded to the facing material. When the meltblown elastic web was stretched in the machine direction as it was bonded to the facing material, the elastic multilayer composite was allowed to retract to form a stretch bonded laminate. The second set of bond rollers were heated to a temperature of about 212 degrees Fahrenheit (about 100 degrees Celsius). The nip pressure within the second nip was also about 150 pounds per linear inch.

A first facing material was unwound into the second nip on a first side of the elastic meltblown material. One of the facings was an aSFL material. A second facing material, a spunbond material, was unwound into the second nip on the side of the elastic meltblown material opposite the first facing material. Table 1 lists the series of examples that was prepared. The series of examples represents a variety of materials having good elastic properties. The samples prepared with 100% KRATON® 2755 polymer demonstrated greater elastic recovery than those that contained the 30% VISTAMAXX™ 2330 olefinic based elastomer.

TABLE 1

| Code | MB Polymer | MB Bonding Pattern | Speed ratio between bonders | Facing 1 | Facing 2 |
|---|---|---|---|---|---|
| 1 | KRATON ® G2755 | pattern unbonded (PUB) | 3 × in MD | aSFL | SB |
| 2 | KRATON ® G2755 | No Bonding (open the nip) | 3 × in MD | aSFL | SB |
| 3 | KRATON ® G2755 | PUB | 3 × in MD | SB | SB |
| 4 | KRATON ® G2755 | No Bonding (open the nip) | 3 × in MD | SB | SB |
| 5 | 70% KRATON ® G2755/30% VISTAMAXX ™ 2330 | PUB | 3 × in MD | aSFL | SB |
| 6 | 70% KRATON ® G2755/30% VISTAMAXX ™ 2330 | No Bonding (open the nip) | 3 × in MD | aSFL | SB |
| 7 | 70% KRATON ® G2755/30% VISTAMAXX ™ 2330 | PUB | 3 × in MD | SB | SB |
| 8 | 70% KRATON ® G2755/30% VISTAMAXX ™ 2330 | No Bonding (open the nip) | 3 × in MD | SB | SB |
| 9 | 70% KRATON ® G2755/30% VISTAMAXX ™ 2330 | PUB | 4 × in MD | SB | SB |

While the embodiments of the invention disclosed herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. An elastic multilayer composite comprising:
a first extensible facing material; and,
an elastic layer attached to the facing material, wherein the elastic layer comprises a continuous bonded region defining a plurality of discreet, fibrous regions being less bonded than the continuous bonded region, and further wherein the extensible facing does not have a continuous bonded region corresponding to the elastic layer continuous bonded region.

2. The elastic multilayer composite of claim 1, wherein the continuous bonded region is a continuous film.

3. The elastic multilayer composite of claim 1, wherein the elastic layer is positioned between and attached to the first extensible facing material and a second extensible facing material.

4. The elastic multilayer composite of claim 1, wherein the first facing material comprises a breathable film.

5. The elastic multilayer composite of claim 3, wherein the second extensible facing material is a nonwoven fabric.

6. The elastic multilayer composite of claim 1, wherein the elastic layer is an extruded meltblown web.

7. The elastic multilayer composite of claim 3, wherein the second facing material comprises a nonwoven fabric.

8. The elastic multilayer composite of claim 1, wherein the elastic multilayer composite is extensible and elastic in the machine direction.

9. The elastic multilayer composite of claim 1 wherein the elastic multilayer composite is extensible and elastic in the cross-machine direction.

10. A method of making an elastic multilayer composite comprising the steps of:
forming an elastic fibrous fabric;
feeding the elastic fibrous fabric into a nip defined between opposedly positioned first and second rollers, said first roller having a patterned outer surface and said second roller having a smooth outer surface;
bonding the elastic fibrous fabric to form on a surface thereof a continuous bonded region defining a plurality of discrete fibrous regions to form a pattern unbonded elastic sheet;
attaching a first facing material to the pattern unbonded elastic sheet.

11. The method of claim 10 further comprising the step of stretching the pattern unbonded elastic sheet by from about 10% to about 500% prior to attaching the first facing material to the pattern unbonded elastic sheet.

12. The method of claim 10 wherein the first facing material comprises a film.

13. The method of claim 12 wherein the film is breathable.

14. The method of claim 10 further comprising the step of necking the first facing material prior to attaching the first facing material to the pattern unbonded elastic sheet.

15. The method of claim 10 further comprising bonding a second facing material to the pattern unbonded elastic sheet wherein the pattern unbonded elastic sheet is positioned between the first and second facing materials.

16. The method of claim 10, wherein the elastic fibrous fabric is an extruded meltblown web.

17. The method of claim 12 wherein the film is slit or apertured.

18. The method of claim 10 wherein the bonding is accomplished by application of heat or pressure.

19. The method of claim 11 wherein the stretching is in the machine direction.

20. The method of claim 10 further comprising the step of stretching the elastic fibrous fabric by from about 10% to about 500% prior to bonding the elastic fibrous fabric to form on a surface thereof a continuous bonded region defining a plurality of discrete fibrous regions to form a pattern unbonded elastic sheet.

21. An elastic multilayer composite produced by the method of claim 10.

22. An article selected from the group consisting of personal care products, safety garments, and medical products comprising the composite of claim 21.

* * * * *